(12) United States Patent
Du (10) Patent No.: US 11,825,928 B2
(45) Date of Patent: Nov. 28, 2023

(54) METHOD OF RECOMMENDING COSMETICS BASED ON MELANIN INDEX AND HEMOGLOBIN INDEX AND DEVICE THEREOF

(71) Applicant: COCORY Color Research Institute, Inc., Daejeon (KR)

(72) Inventor: Yong Hyeung Du, Yongin-si (KR)

(73) Assignee: COCORY Color Research Institute, Inc., Daejeon (KR)

( * ) Notice: Subject to any disclaimer, the term of this patent is extended or adjusted under 35 U.S.C. 154(b) by 0 days.

(21) Appl. No.: 18/015,518

(22) PCT Filed: Jul. 16, 2021

(86) PCT No.: PCT/KR2021/009186
§ 371 (c)(1),
(2) Date: Jan. 10, 2023

(87) PCT Pub. No.: WO2022/015104
PCT Pub. Date: Jan. 20, 2022

(65) Prior Publication Data
US 2023/0189964 A1    Jun. 22, 2023

(30) Foreign Application Priority Data
Jul. 16, 2020    (KR) .................. 10-2020-0088307

(51) Int. Cl.
*A61B 5/00*        (2006.01)
*G06T 7/00*        (2017.01)
(Continued)

(52) U.S. Cl.
CPC .......... *A45D 44/005* (2013.01); *A61B 5/442* (2013.01); *A61B 5/443* (2013.01); *A61B 5/7435* (2013.01);
(Continued)

(58) Field of Classification Search
CPC .................. A45D 44/005; A45D 2044/007; A61B 5/442; A61B 5/443; A61B 5/7435;
(Continued)

(56) References Cited

U.S. PATENT DOCUMENTS

| 2010/0185064 A1* | 7/2010 | Bandic ................ A61B 5/444 600/306 |
| 2019/0295728 A1* | 9/2019 | Jeong .................... G05B 15/02 |
| 2020/0342594 A1* | 10/2020 | Dissanayake .......... G16H 30/20 |

FOREIGN PATENT DOCUMENTS

| KR | 10-2010-0096393 A | 9/2010 |
| KR | 10-2015-0093332 A | 8/2015 |

(Continued)

OTHER PUBLICATIONS

Takiwaki. "Measurement of Skin Color: Practical Application and Theoretical Considerations." The Journal of Medical Investigation, vol. 44, 1998, pp. 121-126 (Year: 1998).*

(Continued)

*Primary Examiner* — Jon Chang
(74) *Attorney, Agent, or Firm* — Park, Kim & Suh, LLC (57) ABSTRACT

The present disclosure relates to a method of recommending cosmetics based on a melanin index and a hemoglobin index and a device thereof, and more particularly to a method for implementing quantification and standardization based on hemoglobin and melanin indexes from personal color consulting, which conventionally done offline based on a color index (Lab index) and has high result variability depending on personal experience or knowledge of a consultant and recommending cosmetics based on the quantification and standardization. The method includes measuring a hemoglobin index and a melanin index of skin and providing a measured value, classifying the measured hemoglobin index and melanin index of the skin into one of a plurality of categories based on a predetermined reference, and recom- (Continued)

mending cosmetics suitable for a color or condition of the skin corresponding to the measured and classified hemoglobin index and the melanin index of the skin, wherein a category of the color of the skin is classified into 4 seasonal categories including a spring type, a summer type, an autumn type, and a winter type.

2 Claims, 8 Drawing Sheets

(51) Int. Cl.
*G06T 7/90* (2017.01)
*A45D 44/00* (2006.01)

(52) U.S. Cl.
CPC ...... *G06T 7/0012* (2013.01); *A45D 2044/007* (2013.01); *G06T 7/90* (2017.01); *G06T 2207/10024* (2013.01); *G06T 2207/30088* (2013.01); *G06T 2207/30201* (2013.01)

(58) Field of Classification Search
CPC ....... A61B 5/0075; A61B 5/1032; A61B 5/00; A61B 5/0077; G06T 7/0012; G06T 2207/10024; G06T 2207/30088; G06T 2207/30201; G06T 7/90; G06Q 30/06; G06Q 30/0631; G06Q 30/0641
See application file for complete search history.

(56) References Cited

FOREIGN PATENT DOCUMENTS

| KR | 10-2015-0098130 A | 8/2015 |
| KR | 10-2015-0105771 A | 9/2015 |
| KR | 10-1852511 B1 | 4/2018 |
| KR | 10-2018-0130778 A | 12/2018 |
| KR | 10-2019-0093040 A | 8/2019 |

OTHER PUBLICATIONS

Alashkar et al. "Rule-Based Facial Makeup Recommendation System." 12th IEEE International Conference on Automatic Face & Gesture Recognition, May 30, 2017, pp. 325-330 (Year: 2017).*
International Search Report in International Application No. PCT/KR2021/009186, dated Oct. 25, 2021, 2 pages.

* cited by examiner

| DIVISION | MOISTURE | OIL | pH | MOISTURE EVAPORATION | ELASTICITY | MELANIN | ERYTHEMA |
|---|---|---|---|---|---|---|---|
| MOISTURE | 1 | | | | | | |
| OIL | .122* | 1 | | | | | |
| pH | -.055 | -.050 | 1 | | | | |
| MOISTURE EVAPORATION | -.118* | -.092 | -.044 | 1 | | | |
| ELASTICITY | .101 | -.116 | -.016 | -.211*** | 1 | | |
| MELANIN | -.045 | .226*** | -.018 | .045 | -.059 | 1 | |
| ERYTHEMA | -.083 | -.123* | .123* | .280*** | -.069 | .100 | 1 |

*$p<.05$. $p<.01$. *$p<.001$

<PERSON CORRELATION COEFFICIENT OF FACIAL SKIN CONDITION MEASUREMENT INDEX (N=304)>

METHOD OF RECOMMENDING COSMETICS BASED ON MELANIN INDEX AND HEMOGLOBIN INDEX AND DEVICE THEREOF

CROSS-REFERENCE TO RELATED APPLICATIONS

This application is a National Phase Application of PCT International Application No. PCT/KR2021/009186, which was filed on Jul. 16, 2021, and which claims priority from Korean Patent Application No. 10-2020-0088307 filed on Jul. 16, 2020. The disclosures of the above patent applications are incorporated herein by reference in their entirety.

TECHNICAL FIELD

The present disclosure relates to a method of recommending cosmetics based on a melanin index and a hemoglobin index and a device thereof, and more particularly to a method for implementing quantification and standardization based on hemoglobin and melanin indexes from personal color consulting, which conventionally done offline based on a color index (Lab index) and has high result variability depending on personal experience or knowledge of a consultant and recommending cosmetics based on the quantification and standardization.

BACKGROUND ART

Personal color is currently applied to all beauty fields, but it does not approach an essential part of skin condition improvement.

A personal color coaching process measures qualitative characteristics with a psychological projection scheme using personality color, subjective tone, and image scale that reveal an emotional side of a human being. In the past, diagnosis has been made depending on visual perception and subjective determination of a consultant using only color fabrics. As a result, the personal color varies depending on a condition of the consultant during diagnosis, or there is no objective indicator for personal color diagnosis, and thus the accuracy is disadvantageously low. To supplement this, a need for digital quantification and scientific statistical processing of personal color has been raised.

Cited Reference 1: Korean Patent Publication No. 10-2010-0096393 (published on Sep. 2, 2010)
Cited Reference 2: Korean Patent Publication No. 10-2015-0093332 (published on Aug. 18, 2015)

DISCLOSURE

Technical Problem

The present disclosure is to solve these problems, and in detail, relates to a cosmetic recommendation method based on quantification and standardization of personal consulting, which are implemented based on a melanin index and a hemoglobin index.

Technical Solution

To achieve the objective, the present disclosure provides a method of recommending cosmetics based on a melanin index and a hemoglobin index, including measuring a hemoglobin index and a melanin index of skin and providing the measured indexes, classifying the measured hemoglobin index and melanin index of the skin into one of a plurality of categories based on a predetermined reference, and recommending cosmetics suitable for a color or condition of the skin corresponding to the measured and classified hemoglobin index and the melanin index of the skin, wherein a category of the color of the skin is classified into 4 seasonal categories including a spring type, a summer type, an autumn type, and a winter type.

The method may further include calculating the condition of the skin matching a combination of the hemoglobin index and the melanin index based on the measured hemoglobin index and melanin index of the skin, the calculated condition of the skin being calculated by digitizing dryness/oiliness, elasticity/inelasticity, and sensitivity/insensitivity, and recommending basic cosmetics based on the calculated condition of the skin.

The method may further include providing a Lab (L: Lightness, a: redness, and b: yellowness) index of the color of the skin matching the hemoglobin index and the melanin index, and recommending color cosmetics based on the Lab index of the color of the skin.

The present disclosure provides a device for recommending cosmetics based on a melanin index and a hemoglobin index, including a camera configured to photograph skin, a communicator configured to transmit a photo of the photographed skin to an external database server, and receive a melanin index and a hemoglobin index that are calculated from the photo of the photographed skin, and information on cosmetics recommended based on the calculated melanin index and hemoglobin index, and a controller configured to control a display to display the calculated melanin index and hemoglobin index, and information on cosmetics recommended based on the calculated melanin index and hemoglobin index, wherein the measured hemoglobin index and melanin index of the skin displayed on the display are classified into one of a plurality of categories based on a predetermined reference and are displayed, the recommended cosmetics displayed on the display are cosmetics suitable for a color or condition of the skin corresponding to the hemoglobin index and melanin index of the skin, and a category of the color of the skin based on the measured hemoglobin index and melanin index of the skin is classified into 4 seasonal categories including a spring type, a summer type, an autumn type, and a winter type.

The display may display the condition of the skin matching a combination of the hemoglobin index and the melanin index, calculated based on the measured hemoglobin index and melanin index of the skin, the calculated condition of the skin is calculated by digitizing dryness/oiliness, elasticity/inelasticity, and sensitivity/insensitivity, and the display displays information on basic cosmetics recommended based on the calculated condition of the skin.

The display provides a Lab (L: Lightness, a: redness, and b: yellowness) index of the color of the skin matching the measured hemoglobin index and melanin index of the skin, and display the display displays information on color cosmetics recommended based on the Lab index of the color of the skin.

Advantageous Effects

According to the present disclosure, a melanin index and a hemoglobin index may be quantified and a skin condition and skin color of a person may be conveniently recognized based on the quantified indexes.

Information on color cosmetics suitable for the skin color of the person or basic cosmetics suitable for the skin condition of the person may be recommended based on the above information, thereby advantageously increasing convenience of choosing cosmetics and improving user satisfaction.

BEST MODE

As the present disclosure allows for various changes and numerous embodiments, particular embodiments will be illustrated in the drawings and described in detail in the written description.

However, this is not intended to limit the present disclosure to particular modes of practice, and it is to be appreciated that all changes, equivalents, and substitutes that do not depart from the spirit and technical scope of the present disclosure are encompassed in the present disclosure.

The terms such as "first" and "second" are used herein merely to describe a variety of constituent elements, but the constituent elements are not limited by the terms.

The terms are used only for the purpose of distinguishing one constituent element from another constituent element.

For example, a first element may be termed a second element and a second element may be termed a first element without departing from the teachings of the present disclosure.

As used herein, the term "and/or" includes any and all combinations of one or more of the associated listed items.

It will be understood that when an element, such as a layer, a region, or a substrate, is referred to as being "on", "connected to" or "coupled to" another element, it may be directly on, connected or coupled to the other element or intervening elements may be present.

In contrast, when an element is referred to as being "directly on," "directly connected to" or "directly coupled to" another element or layer, there are no intervening elements or layers present.

The terms used herein is for the purpose of describing particular embodiments only and is not intended to be limiting of the present disclosure.

The singular forms "a," "an" and "the" are intended to include the plural forms as well, unless the context clearly indicates otherwise.

It will be further understood that the terms "comprises" or "comprising" when used in this specification, specify the presence of stated features, integers, steps, operations, elements, or components, but do not preclude the presence or addition of one or more other features, integers, steps, operations, elements, components, or groups thereof.

Hereinafter, the present disclosure will be described in detail by explaining exemplary embodiments of the disclosure with reference to the attached drawings. The same reference numerals in the drawings denote like elements, and a repeated explanation thereof will not be given.

The skin together with nerves, blood vessels, sweat glands, and sebaceous glands constitutes the largest organ, an integumentary system, which accounts for about 16% of a human body, and a function thereof includes body protection, sensation, temperature control, absorption and secretion, excretion of waste, storage of fat in subcutaneous tissue, and synthesis of vitamin D, and is affected by biological causes such as bacteria, fungi, and viruses, physical causes such as trauma, heat, and radiation, chemical causes caused by endogenous or exogenous chemical substances, and immunological causes such as antigen-antibody reactions.

The skin is usually composed of epidermis, dermis, and subcutaneous.

Figure 1:
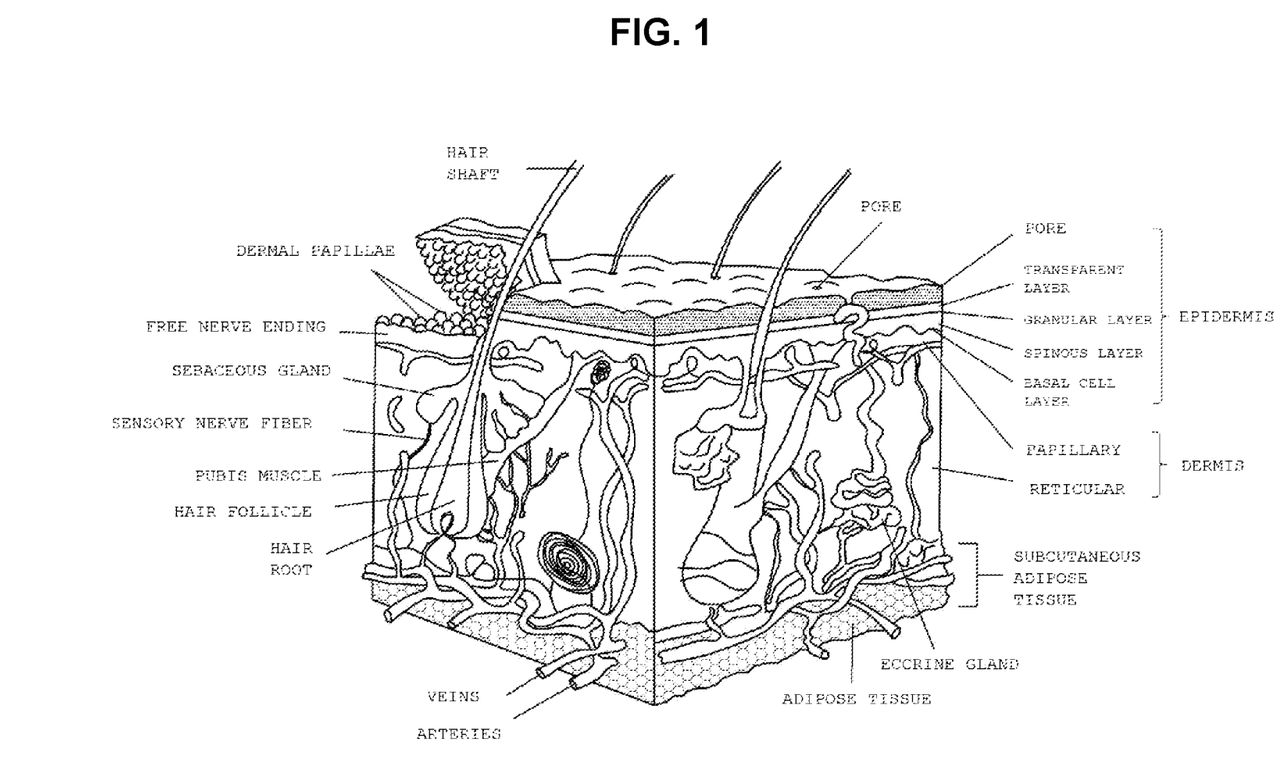
FIG. 1 shows the structure of the skin.

FIG. 1 shows the structure of the skin.

The epidermis is the outermost layer of the skin and each layer includes a basal cell layer composed of cuboidal-shaped basal cells, a spinous layer containing desmosomes, a granular layer containing keratohyaline granules, and a stratum corneum that functions as a barrier surrounded by a cell envelope, and the structure and function of cells change according to these layers. In addition, keratinocytes, Melanocytes, Langerhans cells, and Merkel cells exist in the epidermis.

The dermis is a connective tissue located between the epidermis and the subcutaneous, and is divided into a papillary located as an upper part and a reticular located as a lower part and provides the flexibility, elasticity and tension of the skin to structurally support the epidermis. The dermis is involved in the thickness of the skin and is mainly composed of the fibroblast composed of collagen fibers and elastin fibers. In addition, there are mast cells and macrophages, and there are capillary vessels, lymphatic vessels, nerves, sebaceous glands, and sweat glands that are capable of performing important functions of the skin such as skin nutrition, sensation, and waste excretion.

The subcutaneous is located between the dermis, the muscles, and bones and varies greatly depending on the individual body part. The subcutaneous fat tissue is distinct from the fibrous connective tissue under the reticular, but is functionally closely related to the dermis. In addition, the subcutaneous protects a living body and regulates body temperature.

A skin condition is determined based on a sebum secretion condition, a moisturizing condition, a skin tissue condition, a pore condition, and an elasticity level, is classified depending on a sensitivity degree, a degree of blood circulation, a pigmentation degree, complexion, and a degree of skin texture, and in order to evaluate skin conditions, skin texture, oil/moisture, epidermis water loss, elasticity, erythema, and degree of melanin, which are determinants of skin condition, act as important factors.

Skin moisture is a plasticizer of keratin and is an important component that increases the flexibility of the stratum corneum, prevents cracking, makes the stratum corneum well bent, and increases the activity of enzymes involved in an epidermis exfoliation process. In the dry skin, a moisture content of an upper part of the epidermis is reduced below normal, and as a result, a skin surface becomes rough, wrinkles occur, and a clinical picture in which keratinocytes are eliminated is shown. The moisture content of the skin surface has a great effect on a water holding capacity according to a natural moisturizing factor (NMF) and intercellular lipid present in the stratum corneum, and when the NMF and the intercellular lipid do not exist properly, the moisture content becomes insufficient. Moisture in the skin is reduced by the amount of smoking and excessive stress, a physical state, UV rays, dry weather, and a high temperature of face wash result in skin dryness, and as skin tightening increases, skin aging such as fine wrinkles is accelerated, and accordingly, the moisture in the skin acts as an important factor in determining a skin condition.

Oil or sebum of the skin is secreted from the sebaceous glands to the skin surface in an amount of 1 to 2 g per day. Components of sebum include triglycerides, wax, squalen, cholesterol, and cholesterol esters. In sebum, triglyceride is classified into free fatty acid, monoglyceride, and diglyceride by lipase, which is a lipid degrading enzyme. Sebum secretion varies depending on hormones, gender, age, body part, temperature, time, and seasonal factors. The secreted oil and the moisture secreted from the sweat glands combine to form a sebaceous membrane, which prevents skin from drying out and makes the skin moist and smooth. Sebum is hydrolyzed by triglycerides to form a sebaceous membrane with free fatty acids to protect the skin from external stimuli and to maintain smooth skin and control moisture retention, and thus is a very important factor in identifying skin conditions.

Skin elasticity refers to the property of a material to return to an original state thereof after being deformed by an external force, and may vary depending on the fidelity and moisturizing state of collagen and elastin fiber tissues, which are constituent materials of the dermis. Collagen forms a woven form (reticular structure) with elastin, and contains sufficient moisture, which determines a state of skin elasticity, and the elastin fiber is composed of 90% of amorphous insoluble protein (elastin) and microfibrillar protein. Wrinkles and loss of elasticity mean that functions of collagen fibers and elastin fibers in the dermis are weakened, and skin elasticity changes according to aging, ultraviolet rays, and water retention.

Erythema is one of typical skin reactions induced by ultraviolet rays, particularly ultraviolet B, and refers to a phenomenon observed with the naked eye when the amount of blood in the skin blood vessels increases by 38% or more as the skin becomes red. In the case of facial flushing, the skin is always kept in an excited state because more than a certain amount of blood flow flows to the skin surface. Melanin and erythema are used as a factor to evaluate an individual skin color.

The skin pigments visible on the skin surface are the result of melanin being transferred to keratinocytes by various factors from melanocytes in skin cells and accumulated in the epidermis. With regard to the melanin pigment, tyrosine is oxidized by tyrosinase in the melanocyte present in the basal cell layer of the epidermis to produce DOPA and to finally produce the melanin pigment.

Melanin is classified into dark brown eumelanin and reddish yellow pheomelanin, and a melanocortin-1 receptor regulates production of eumelanin or pheomelanin in melanin cells.

Melanin has ability to protect a sensitive molecular structure of the skin by absorbing all UV rays and to eliminate free radicals (which cause DNA damage), and prevents essential vitamins such as folic acid from being destroyed.

Darker skin color means larger and more melanosomes, and a difference in the incidence of skin cancer according to presence or absence of melanin is greater, and the incidence of fatal melanoma among skin cancers is higher in light skin, freckles, and red hair.

Hemoglobin is a pigment that is a source of blood color and is dark red, and anemia is diagnosed based on the amount of hemoglobin. Hemoglobin transports oxygen throughout a living body.

The amount of melanin does not change in a short period of time, but the amount of hemoglobin is related to blood flow, and thus is relatively easily changed in a short period of time by factors such as stimulation, temperature, physical condition, and psychological condition.

There are various classification references for skin type, but the present disclosure provides three references, and the skin type is classified into dry and oily skin, sensitive skin and insensitive skin, and elastic skin and non-elastic skin.

Dry skin and oily skin according to skin moisturizing are as follows.

Dry skin, as a dictionary meaning, simply refers to a state in which there is insufficient or no moisture in the skin (less than 10%), and normally, has grayish white skin color, and has many curves. Oily skin is a skin type that is easily greasy and gets dirty quickly due to a high amount of sebum secretion.

A dry and oily skin type is mainly determined depending on a barrier function of the skin stratum corneum, and this skin barrier helps the skin retain moisture and autonomously generate and secrete sebum. The damaged barrier becomes dry or sensitive when moisture in the skin evaporates, resulting in dry skin. In addition, the abnormality of the stratum corneum lamellar structure, which is different from a change in the composition and content of lipids between keratinocytes, causes weakening of a stratum corneum function, and consequently causes dry skin.

A degree of dryness and dehydration of the skin of the stratum corneum may be known by transepidermal water loss (TEWL), and when the barrier of the skin stratum corneum is exposed to various environmental substances such as detergents, acetone, chlorine, and other chemicals or is submerged in water for a long time, the barrier of the skin is destroyed, causing dryness by evaporation of skin moisture. Therefore, it is important to restore the skin barrier in the case of dry and oily skin types according to skin moisturizing.

Sensitive skin and insensitive skin according to skin sensitivity will be described below.

Sensitive skin has thin and delicate skin tissue, and thus resistance to external stimuli is weak, physical and chemical reactions are large, and sensitive skin often appears in allergic skin. In other words, sensitive skin reacts negatively and sensitively to external factors such as cold air, heat, temperature change, wind, as well as pollution and excessive use of special materials. In addition, sensitive skin has a great connection with psychological and mental things, and thus reacts sensitively to chemical and external environmental stimuli. Resistant skin is the skin that strongly protects the skin from allergens and irritants by providing a barrier around the skin cells in the tightly bound stratum corneum.

Baumann classifies sensitive skin as an acne subtype in which blackheads or whiteheads occur, a rosacea subtype in which persistent reddening symptoms and facial redness and feeling of heat occur, a stingy subtype in which burning or stinging of the skin occurs, and an allergic subtype in which redness of the skin, itching and peeling symptoms occur. As these sensitive skin subtypes commonly have an inflammatory reaction, it is important to reduce inflammation when managing sensitive skin.

Non-elastic skin and elastic skin according to skin aging are as follows.

Skin aging is divided into endogenous and extrinsic causes. Endogenous aging is a phenomenon caused by an individual genetic program and is not avoided or controlled, and extrinsic aging is caused by smoking, pollution, malnutrition, sun exposure, etc. Histological changes of the skin include atrophy of the epidermis, flattening of a border between the epidermis and the dermis, and atrophy of the dermis. In addition, as the skin ages, the role of oil glands and sweat glands decreases, the amount of moisture in cells decreases, the thickness of the skin thickens, and collagen and elastin inside the dermis tissue loosen, resulting in wrinkles due to abnormal elastin fibers. In addition, pigmentation increases and circulatory function decreases due to a decrease in UV defense ability, and thus the skin easily reacts to allergies or stimuli. For wrinkle prevention, retinoid, vitamin C, copper peptide, etc. need to be used, and this increases collagen synthesis and elastin production, and thus is effective for aging skin.

In classification of skin type, significant variables of dry/oily are melanin and oil, significant variables of elasticity/inelasticity are related to moisture evaporation, and significant variables of sensitive/insensitive have a significant correlation with erythema. The correlation is shown in a table of FIG. 2.

Figure 2:
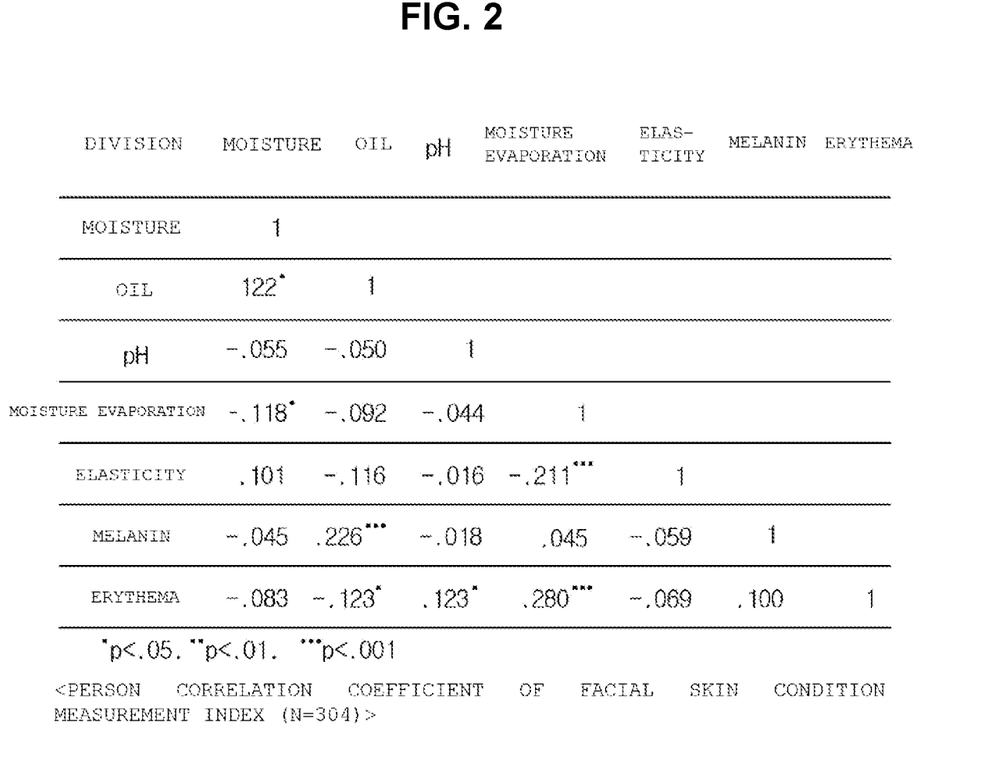
FIG. 2 is a chart digitizing a correlation of measurement indicators of a facial skin condition.

It shows that the state of the skin barrier present in the stratum corneum is determined by the amount of sebum controlled by melanin-stimulating hormone, the amount of water secreted from the eccrine glands, and the moisture evaporation affected by the amount of oil and water.

If an oil content is high, the amount of moisture and the amount of melanin are high, if the moisture evaporation is high, an erythema phenomenon occurs highly, and if the moisture evaporation is low, the amount of moisture, the amount of oil, and elasticity are high.

Eventually, the skin barrier loses a protective function of the sebaceous membrane due to excessive oil, insufficient or excessive moisture, and excessive moisture evaporation, and accordingly, it may be inferred that this is a major factor in changing skin conditions such as erythema, wrinkles, skin aging, decreased elasticity, increased sensitivity, enlarged pores, acne, and melisma.

It is deemed that a negative (−) correlation between oil and erythema in which, as an oil content is reduced, the amount of moisture is reduced and the amount of erythema is increased due to the reduced skin barrier, is achieved, and the oil content of the skin, that is, a level of sebum production, is a very important factor in determining a skin condition and a skin type.

As for a correlation between oil and melanin, it may be observed that sebaceous gland formation and sebum production are reduced in genetically modified mice lacking the Melanocortin-5 receptor, and Melanocortin contains melanin-stimulating hormone, is also found in human sebaceous glands, and regulates sebum production.

Therefore, it may be seen that a positive (+) correlation between oil and melanin is achieved, and thus the more oil secreted, the higher the correlation with melanin. As a result, a melanin index may be a high representative index that is likely to be used as a single index to identify various skin conditions.

Therefore, skin color or skin condition may be quantified by melanin (M) and hemoglobin (Hb) indices, and human skin color has all colors of red, yellow, brown, or blue.

Red is mainly from oxidized hemoglobin, yellow is mainly from a pigment called carotenoid, blue is from reduced hemoglobin in veins, and brown is mainly from melanin produced in melanocytes. Lanin is the most important pigment among factors that determine the skin color of a person.

Figure 3:
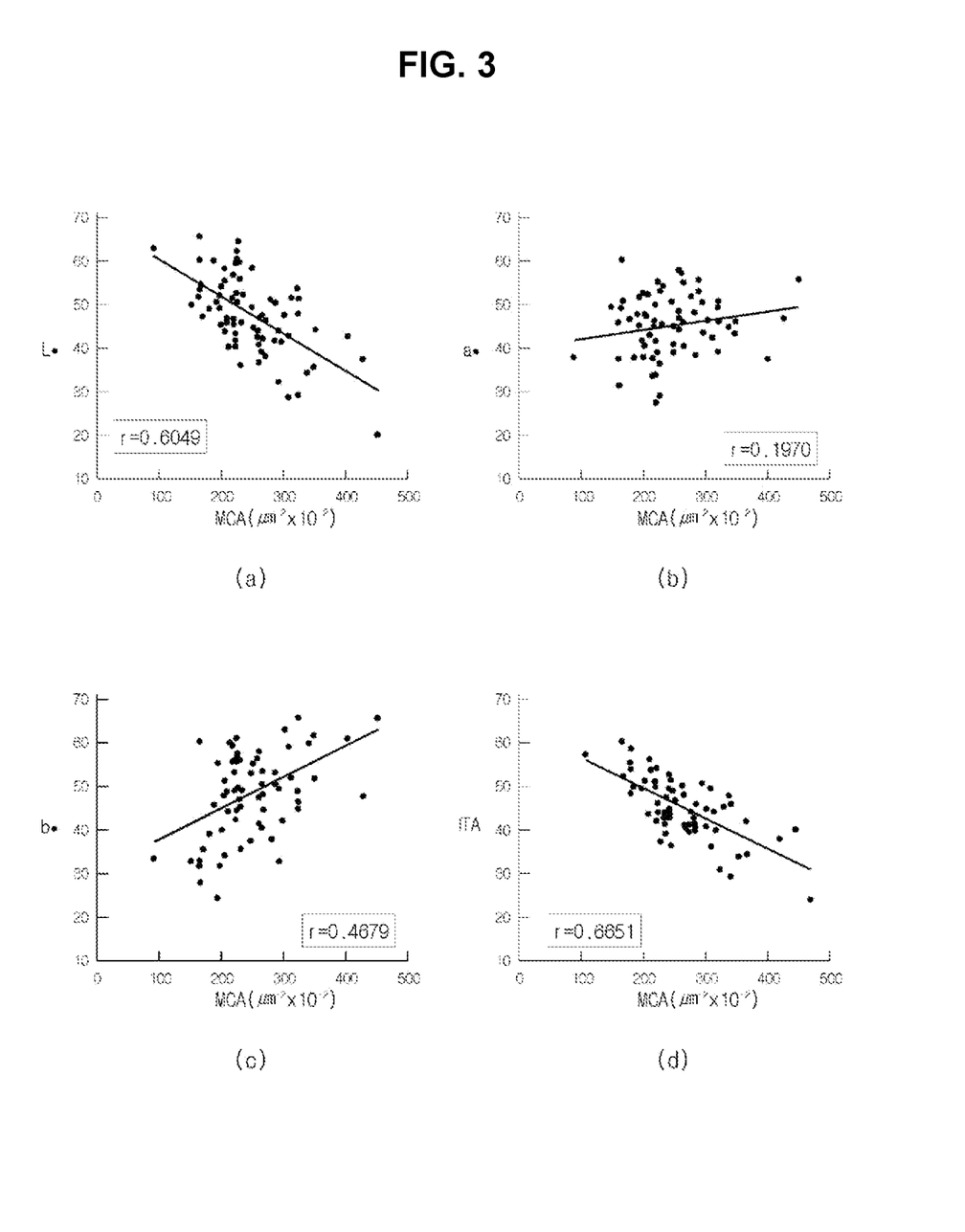
FIG. 3 shows a correlation between a Lab index, and an ITA and a MCA.

FIG. 3 shows a correlation between a measured value of a color difference meter of a melanin covering area (MCA) and the amount of melanin.

The color difference meter is also called a Lab index. The Lab is an internationally standardized color system standardized by Colmmission Internationale d'Eclairage (CIE) in 1976, and is a color concept based on the anti-color theory that red, green, blue and yellow in all colors are not perceived at the same time.

In general, the color difference meter is indicated as CIELAB or L*a*b* and is used in Photoshop in a Lab mode. This is a color system that is a standard for increasing compatibility with various color systems, includes all colors to be perceived by the human eye, and simultaneously, is a color system that enables the same color to be expressed regardless of the color characteristics of digital equipment.

Since the Lab is a device independent color system regardless of the color characteristics of output, display, and input devices, it is a profile connection space that is the center of connecting colors between devices in CMS. In addition, the Lab is the most widely used color system for expressing the color of an object internationally, and designers or those who conduct research on color already use the Lab in general.

A channel L in the Lab mode is an abbreviation of Lightness and refers to brightness, which is a degree of lightness and darkness of an image. With regard to a channel a* that means a correlation between green and red, green is shown toward a negative side, and red is shown toward a positive side, and with regard to a channel b* that means a correlation between blue and yellow, blue is shown toward a negative side, and yellow is shown toward a positive side.

In general, a* refers to redness, and b* refers to yellowness.

As seen from the graph of FIG. 3, the correlation between the measured value of the color difference meter of the melanin covering area (MCA) and the amount of melanin may be obtained by comparison based on a value L* (whiteness), a value a* (redness), a value b* (yellowness), Individual Typology Angle (ITAo), and ArcTan ((L*−50)/b*)×180/π), and the results may be 0.6049, 0.1970, 0.4679, and 0.6651, respectively, and accordingly, it may be seen that melanin has a high correlation with brightness (L) and yellowness (b).

As a result, since there is a close correlation between the amount of melanin and skin color, a melanin quantification method in keratinocytes may be used in many fields, and the research results show that the amount of melanin is determined by coordinates of L (brightness) and b (yellowness) of a spectrophotometer.

Figure 4:
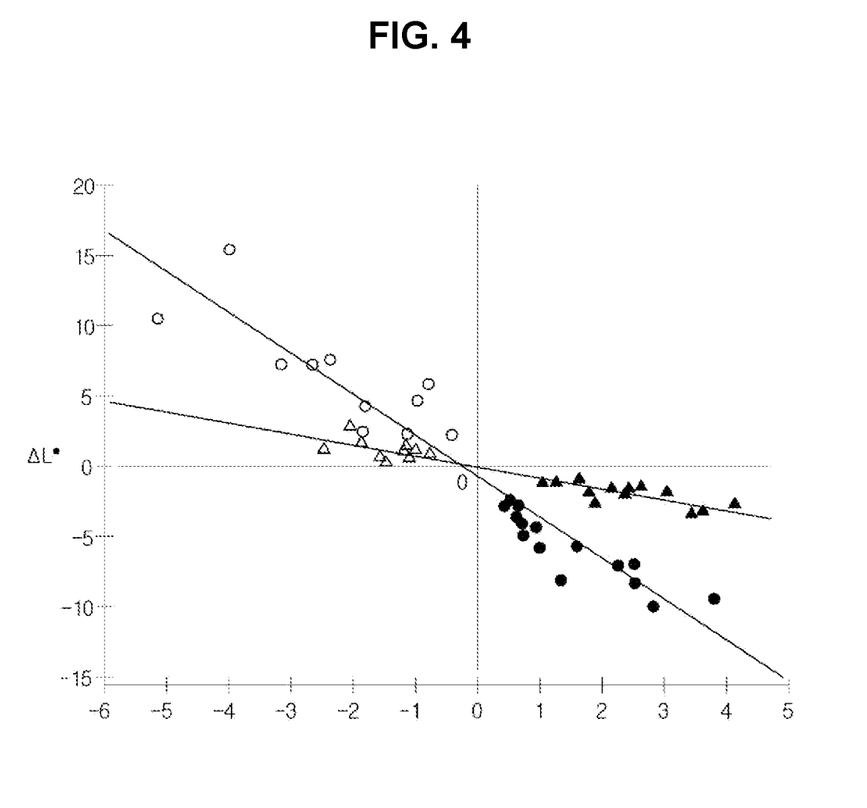
FIG. 4 is a graph showing a correlation between ΔL* and Δa*.

In FIG. 4, a changes in values of Δa* and ΔL* due to a changes in the amount of hemoglobin and melanin may be seen. Both a* and L* are ideal indicators for the changes in the amount of Hb and melanin, respectively.

A change in skin color due to a simultaneous change in the amount of Hb and melanin is most likely to be solved with a two-component vector inherent in the change in Hb or melanin.

Although the amount of hemoglobin (Hb) in the skin is generally estimated in a* units, evaluation of a degree of skin pigmentation or the amount of melanin usually includes L* or similar coordinates of Y in the Yxy system (5±7).

As seen from the research result, melanin may be determined by coordinates of L (brightness) of a spectrophotometer and the amount of hemoglobin may be determined by coordinates of a (redness). From the perspective of color science, the fact that melanin commonly affects brightness shows that skin color is related to the amount of melanin and hemoglobin.

Summarizing the results of the above research, it may be seen that the amount of melanin is seen by coordinates of b* and the amount of hemoglobin is seen by coordinates of a*.

Based on the above description, according to the present disclosure, the amount of melanin and hemoglobin, to be measured in the skin of each individual, may be quantified, a database that correlates with Lab indicators based on the quantified amount may be accumulated, and then when a melanin level and hemoglobin level of the skin for each individual are obtained, appropriate cosmetics (color cosmetics or basic cosmetics) may be recommended.

Figure 5:
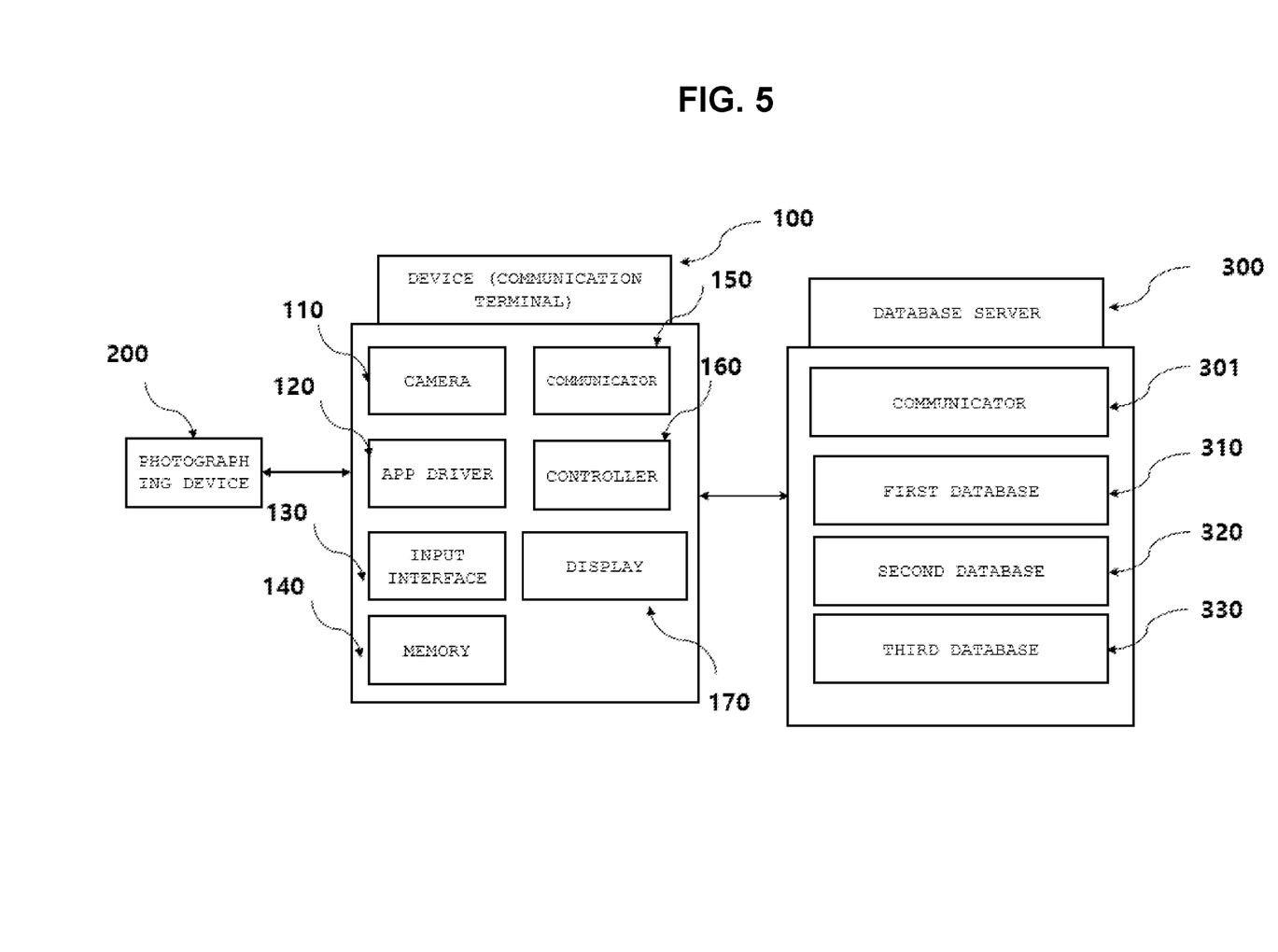
FIG. 5 is a control block diagram of a device or a communication terminal for implementing the present disclosure.
Figure 6:
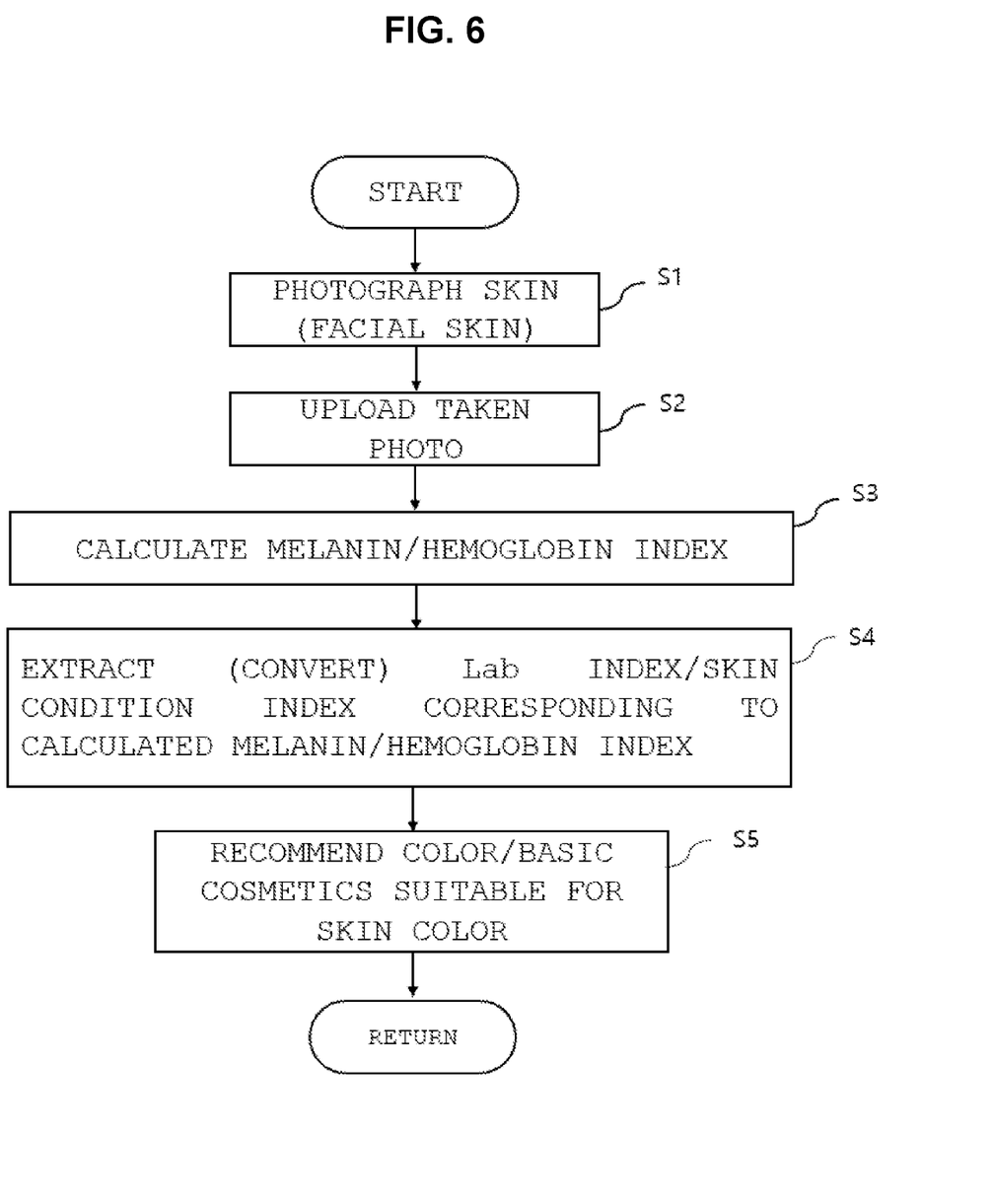
FIGS. 6 and 7 are control flowcharts according to the present disclosure.

As shown in FIGS. 5 and 6, the present disclosure may obtain a melanin level and a hemoglobin level by using a cosmetics recommendation application, which is installed in a communication terminal such as a smartphone or a device 100 and is operated by an app driver 120, and a photographing device 200 to be connected to the communication terminal or a camera 110 in the communication terminal.

A communicator 150 of the communication terminal may be operatively connected to an external database server 300, and the database server 300 may include a communicator 301 and a plurality of databases 310, 320, and 330.

Here, a first database 310 may be a database that contains a melanin level and hemoglobin level related to the color of the skin shown in the photograph or video, and a second database 320 may be a database in which combinations of various melanin levels and a hemoglobin level are matched with Lab indicators.

The second database 320 may include data on skin condition indexes according to various combinations of a melanin level and a hemoglobin level. Here, the skin condition index means information on oiliness/dryness, elasticity/inelasticity, and sensitivity/insensitivity.

When the captured skin photo is uploaded to the application (S2 in FIG. 6), the uploaded photo may be transferred to the database server, a melanin index and a hemoglobin index of the photographed skin may be calculated in the first database 310 and displayed on a display 170 (S3 in FIG. 6), and then the Lab index or the skin condition index that matches the melanin index and hemoglobin index may also be calculated and displayed on the display 170 of the communication terminal (S4 in FIG. 6).

When a user wants to receive a recommendation for cosmetics suitable for his or her skin color or skin condition and touches a recommendation button through an input interface 130 of the communication terminal, information on the corresponding basic cosmetics or color cosmetics may be recommended through information stored in a third database 330 (S5 in FIG. 6).

A controller 160 may display the calculated melanin index and hemoglobin index and information on recommended cosmetics based on the calculated melanin index and hemoglobin index on the display, while the communicator 150 may control the communicator 150 to smoothly communicate with the communicator 301 of the database server.

Figure 7:
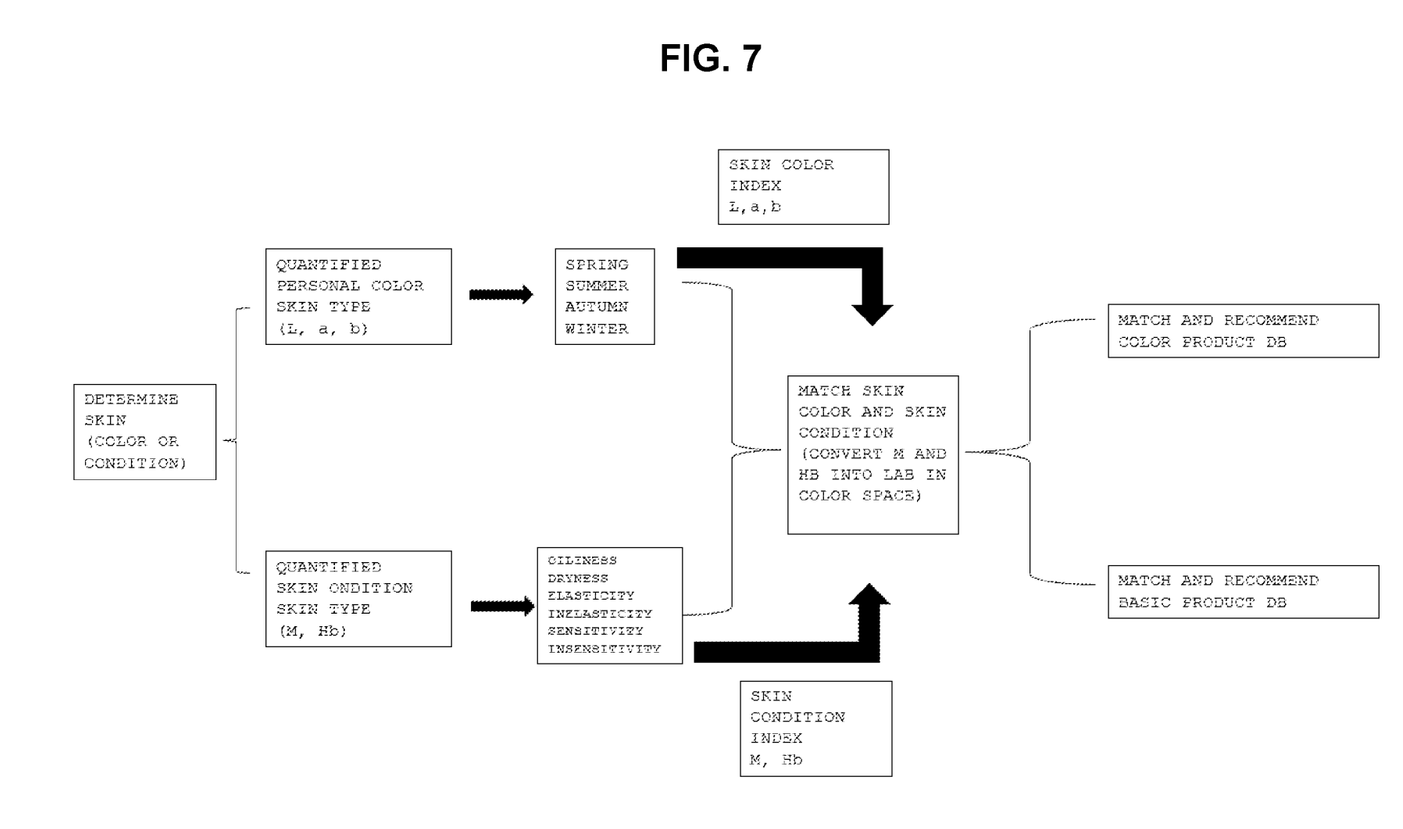

Simplifying this with a diagram shown in FIG. 7, skin is determined by color or condition.

Here, the color of the skin may be determined and classified as a quantified personal color skin type, but may be quantified using the Lab index, and the condition of the skin may be quantified using the quantified melanin index (M) and hemoglobin index (Hb).

The quantified skin color may be re-classified into spring, summer, autumn, and winter, and the quantified skin condition may be classified into oiliness, dryness, elasticity, inelasticity, sensitivity, and insensitivity.

According to the present disclosure, the melanin index (M) and hemoglobin index (Hb), which represent the condition of the skin, may be acquired through a measuring device, etc., and then the values may be matched with the Lab indexes accumulated on the DB, and accordingly, may be used as an indicator representing the skin color.

For example, the melanin index (M) and hemoglobin index (Hb) of the face of a person A may be measured using a skin condition measuring device, the Lab index of the face of the person may be measured using a colorimeter, and the indexes may match each other.

When these measurement operations are performed on a plurality of people and their melanin indexes (M), hemoglobin indexes (Hb), and Lab indexes are connected, a relationship representing predetermined regularity may be established.

Accordingly, when the melanin index (M) and the hemoglobin index (Hb) of a specific person are measured, the skin condition and skin color of the person may be quantified. Therefore, appropriate color cosmetics may be recommended using the quantified skin color index, or basic cosmetics may be recommended using the quantified skin condition.

Table below shows an example showing a relationship of the Lab index, the melanin index (M), and the hemoglobin index (Hb).

TABLE 1

|  | L | a | b |
|---|---|---|---|
| Spring | 65.19 | 14.73 | 20.51 |
| M |  | 144.0 ± 21.5(AU) |  |
| Hb |  | 378.0 ± 19.8(AU) |  |
| Summer | 66.26 | 14.31 | 18.53 |
| M |  | 85.1 ± 12.7(AU) |  |
| Hb |  | 453.3 ± 40.4(AU) |  |
| Autumn | 63.29 | 15.37 | 21.89 |
| M |  | 202.0 ± 6.2(AU) |  |
| Hb |  | 279.3 ± 26.3(AU) |  |
| Winter | 64.63 | 15.34 | 19.65 |
| M |  | 196.8 ± 34.0(AU) |  |
| Hb |  | 356.3 ± 26.0(AU) |  |

As described above, the skin condition is related to the content of oil and moisture, and the skin condition determined by the content of oil and moisture is understood by a relationship between the melanin index and the hemoglobin index.

The skin condition is classified into dryness/oiliness, elasticity/inelasticity, and sensitive/insensitive according to a level of oil and moisture content.

The skin barrier is determined according to a state of a combination of oil and moisture, and is closely related to secretion of the amount of sebum among them. That is, Melanocortin contains melanin-stimulating hormone, is also found in human sebaceous glands, and regulates sebum production.

A degree of oil retention by stimulation of melanin affects formation of sebaceous membrane and increases the amount of water evaporation, which affects skin aging and wrinkles, while erythema is related to blood flow.

Therefore, the amount of melanin and hemoglobin, which are main factors determining skin color, is also related to a skin condition, and the skin condition by a relationship between the amount of melanin and hemoglobin as an example is shown in Table below.

In Table 2, for the melanin index and the hemoglobin index, when the lowest is 0 and the highest is 500, 'Low' may range from 0 to 100, "Mid-low" may range from 101 to 200, "Middle" may range from 201 to 300, "Mid-high" may range from 301 to 400, and "High" may range from 401 to 500.

For oiliness, dryness, elasticity, inelasticity, sensitivity, and insensitivity, when the lowest is 0 and the highest is 100, 'Low' may range from 0 to 20, "Mid-low" may range from 21 to 40, "Middle" may range from 41 to 60, "Mid-high" may range from 61 to 80, and "High" may range from 81 to 100.

TABLE 2

| melanin index | hemoglobin index | oiliness | dryness | elasticity | inelasticity | sensitivity | insensitivity |
|---|---|---|---|---|---|---|---|
| Mid-high | Mid-low | Mid-high | Mid-low | Mid-high | Mid-low | Mid-low | Mid-high |
| Low | Low | Low | High | Low | High | High | Low |
| High | High | High | Low | High | Low | Low | High |
| Mid-low | Mid-high | Mid-low | Middle | Mid-low | Mid-high | Mid-high | Mid-low |

That is, for example, if a skin condition of a person is measured and the melanin index is within the range of 'Mid-high' and the hemoglobin index is within the range of 'Mid-low', the skin condition of the person may be represented as 'Mid-high' of oiliness, 'Mid-high' of elasticity, and 'Mid-high' as insensitivity.

Personal color may be divided into four main type groups, and in detail, may be divided into a spring type, a summer type, an autumn type, and a winter type, like four season classification. In each type, the personal color may be subdivided into three tones including a warm tone, a cool tone, and a neutral tone.

The warm tone is an English expression of the Chinese character for 暖色, and from a point of view of personal color, an exact name of the warm tone corresponds to a yellow base. The yellow base is a base in which the skin color is mainly yellow. Overall, the skin tone is yellow, and there is no redness. The skin tone with a yellowish tinge, which is a yellow base, is often called an apricot skin tone, and overall, a yellowish tinge is felt uniformly, creating a cheerful, healthy, and calm image.

According to the brightness of the skin tone, the skin may be divided into bright and transparent yellow skin, calm yellow skin without complexion, and healthy yellow skin with a copper tint.

Although a perceived image is different depending on skin brightness, a healthy and calm image of yellow color may be equally applicable to warm tone and yellow base. A yellow base with a yellow tinge may make the yellow tinge stand out more by making it feel heterogeneous if a pink color is used to create a more reddish tinge. A coral pink or an orange color may be used to create a lively complexion.

The cool tone is an English expression of the Chinese character for 寒色, which means a cold atmosphere. From a personal color point of view, an exact name of the cool tone corresponds to a blue base. The blue base is a skin base with a reddish skin tone. Overall, in addition to a yellow tinge that Asians have, a red tinge appears on the cheeks and the forehead, and there are many cases of flushing.

A skin tone with a reddish tone, which is a blue base, is also called a cherry-colored skin tone. There is redness on the cheeks or the forehead, and thus an entire face shows red (pink), which makes the complexion look good and makes the skin look clean.

Depending on the brightness of a skin tone, the skin is divided into clear and red skin, fair and soft skin, and cold and dark skin. A perceived image differs depending on the skin brightness, but if the skin has a reddish tone, the skin creates a soft and clear image and a strong and clear image, and this is equally applicable to a cool tone and a blue base.

Blusher is often used to remove the redness or flushing that the skin has. In this case, the redness or flushing may stand out, and thus the redness or flushing may be used as a natural blusher. Makeup may be reduced as much as possible to create a clear and soft image that a person originally has, and light pink or color may be used to highlight one part of the entire face.

The neutral tone has all of the elements of the above warm tone and cool tone. If a person has a yellow tinge of a healthy image as a whole, but has flushing on the cheeks or the skin tone is neither yellow nor red, the skin is diagnosed as the neutral tone.

When both pink lipstick and orange lipstick are applied, neither one of them protrudes unilaterally, and the eyes or hair color are often gray.

Figure 8:
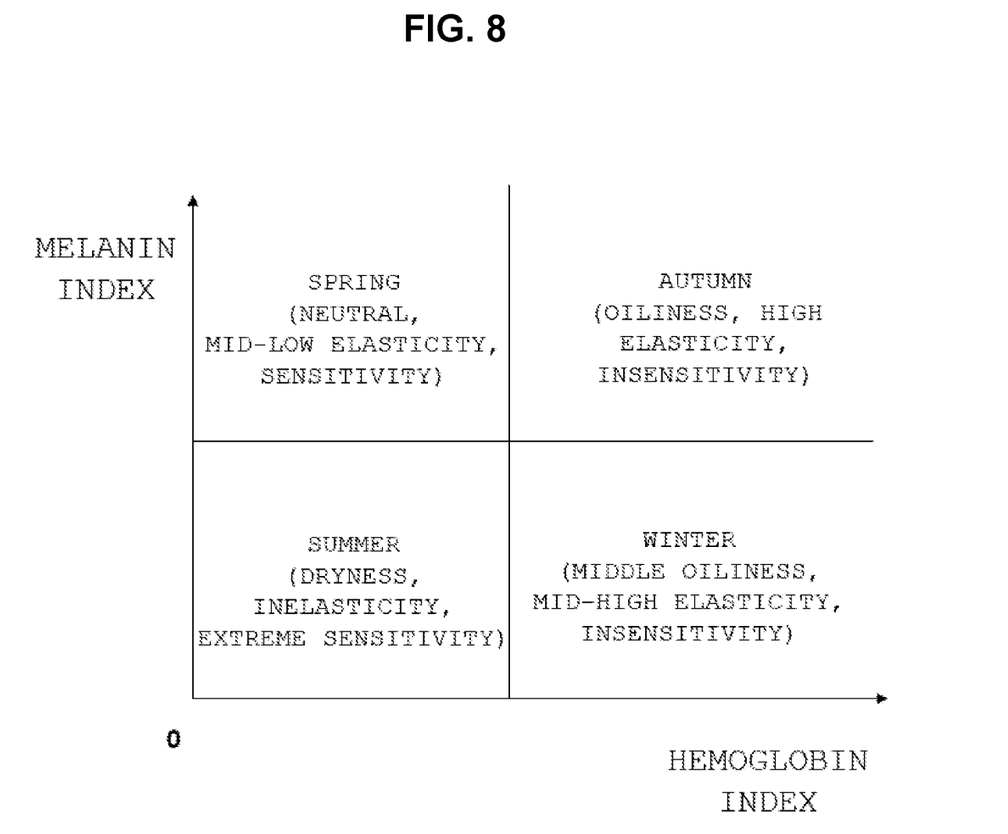
FIG. 8 is a chart showing 4 season classification of colors based on a melanin index and a hemoglobin index according to the present disclosure.

As shown in FIG. 8, when a melanin index is relatively high and a hemoglobin index is low, skin characteristics have neutral, mid-low elasticity, and sensitivity, and in this case, the skin may be classified as a spring type.

When the melanin index is relatively low and the hemoglobin index is low, the skin characteristics have dryness, inelasticity, and extreme sensitivity, and in this case, the skin may be classified as a summer type among the four seasons.

When both the melanin index and the hemoglobin index are relatively high, the skin characteristics have oiliness, high elasticity, and insensitivity, and in this case, the skin may be classified as an autumn type among the four seasons.

When the melanin index is relatively low and the hemoglobin index is high, the skin characteristics have medium oiliness, medium upper elasticity, and insensitivity, and in this case, the skin may be classified as a winter type among the four seasons.

Therefore, a color type of the skin and a condition of the skin may be derived by a combination of the hemoglobin index and the melanin index. According to the present disclosure, a total of 12 personal colors may be classified by combining 4 seasons and 3 tones, and customized color cosmetics may be recommended for each individual, and basic cosmetics for improving the condition of the skin may be advantageously recommended based on the derived skin condition (oiliness/dryness, elasticity/inelasticity, and sensitive/insensitive).

As such, when color cosmetics or basic cosmetics are recommended based on measured values of the hemoglobin index and melamine index and are displayed on a display, link information of a shopping mall that sells the color cosmetics or the basic cosmetics, or testimonials information or an expert opinion may be linked and displayed, thereby promoting user purchase convenience and ensuring reliability.

While the disclosure has been particularly shown and described with reference to exemplary embodiments thereof, it will be understood by those skilled in the art that various changes in form and details may be made therein without departing from the spirit and scope of the disclosure as defined by the appended claims.

Therefore, the scope of the disclosure is defined by the appended claims.

The invention claimed is:

1. A method of recommending cosmetics in a system including a communication terminal and a database server, the method comprising:
   receiving a photo of a skin taken by a user and determining a condition of the skin by extracting a melanin index and a hemoglobin index corresponding to the photo from a first database of the database server;
   classifying the determined condition of the skin into dryness/oiliness, elasticity/inelasticity, and sensitivity/insensitivity based on the extracted melanin index and the hemoglobin index;
   determining a color of the skin by extracting a Lab (L: Lightness, a: redness, and b: yellowness) index corresponding to a combination of the hemoglobin index and the melanin index from a second database of the database server;
   classifying the determined color of the skin into one of four seasonal categories including a spring type, a summer type, an autumn type, and a winter type based on the extracted Lab index; and
   recommending cosmetics based on quantified information stored in a third database of the database server in accordance with the classified color and condition of the skin,
   wherein the recommending cosmetics comprises recommending basic cosmetics based on the classified condition of the skin and recommending color cosmetics based on the classified color of the skin.

2. A device for recommending cosmetics, the device comprising:
   a camera configured to generate a photo of a skin;
   a communicator configured to transmit the photo to an external database server, and to receive a melanin index and a hemoglobin index corresponding to the photo extracted from a first database of the database server, and information on cosmetics recommended based on the extracted melanin index and hemoglobin index; and
   a controller configured to control a display to display the received melanin index and hemoglobin index, and, the received information on cosmetics,
   wherein a condition of the skin is determined by the extracted melanin index and hemoglobin index and the determined condition of the skin is classified into dryness/oiliness, elasticity/inelasticity, and sensitivity/insensitivity based on the extracted melanin index and hemoglobin index,
   wherein a color of the skin is determined by extracting a Lab (L: Lightness, a: redness, and b: yellowness) index corresponding to a combination of the melanin index and the hemoglobin index from a second database of the database server, and the determined color of the skin is classified into one of 4 seasonal categories including a spring type, a summer type, an autumn type, and a winter type,
   wherein the recommended cosmetics displayed on the display comprise:
   color cosmetics recommended based on the classified color of the skin; and
   basic cosmetics recommended based on the classified condition of the skin.

* * * * *